(12) United States Patent
Liu et al.

(10) Patent No.: US 11,090,030 B2
(45) Date of Patent: Aug. 17, 2021

(54) ULTRASOUND APPARATUS AND ULTRASOUND EMISSION METHOD

(71) Applicant: Leltek Inc., New Taipei (TW)

(72) Inventors: Ying-Yi Liu, Taipei (TW); Sheng-Chang Peng, Taipei (TW); Kuo-Ping Liu, Taipei (TW)

(73) Assignee: Leltek Inc., New Taipei (TW)

( * ) Notice: Subject to any disclaimer, the term of this patent is extended or adjusted under 35 U.S.C. 154(b) by 413 days.

(21) Appl. No.: 15/347,798

(22) Filed: Nov. 10, 2016

(65) Prior Publication Data

US 2018/0125454 A1  May 10, 2018

(51) Int. Cl.
  *A61B 8/00* (2006.01)
  *A61B 8/14* (2006.01)
  (Continued)

(52) U.S. Cl.
  CPC .............. *A61B 8/54* (2013.01); *A61B 8/5207* (2013.01); *G01S 15/89* (2013.01); *A61B 8/145* (2013.01); *A61B 8/4494* (2013.01)

(58) Field of Classification Search
  None
  See application file for complete search history.

(56) References Cited

U.S. PATENT DOCUMENTS 5,812,011 A * 9/1998 Hayashi .............. H03K 17/567
                                                327/431
5,844,139 A  12/1998 Miller et al.
(Continued)

FOREIGN PATENT DOCUMENTS

CN  1184474   1/2005
CN  104414681  3/2015
(Continued)

*Primary Examiner* — Angela M Hoffa
*Assistant Examiner* — Younhee Choi
(74) *Attorney, Agent, or Firm* — JCIPRNET

(57) ABSTRACT

An ultrasound apparatus and a method of emitting plane wave are provided. The ultrasound apparatus includes an ultrasound probe, a transceiver circuit, a switch module and a processor. The ultrasound probe has a $1_{st}$ to a $M_{th}$ transducer elements for respectively emitting ultrasound beams to form the plane wave, and the transceiver circuit has a $1_{st}$ to a $N_{th}$ transceiving channels. M, N are positive integers, and M is a multiple of N. During a scanning period, the processor controls the switch module to initially and respectively connect the $1_{st}$-$N_{th}$ transceiving channels to the $1_{st}$-$N_{th}$ transducer elements, such that the $1_{st}$-$N_{th}$ transducer elements successively emit the ultrasound beams. After the ultrasound beam is emitted by the $N_{th}$ transducer element, the processor controls the switch module to respectively connect the $1_{st}$-$N_{th}$ transceiving channels to the $(N+1)_{th}$-$(2N)_{th}$ transducer elements, such that the $(N+1)_{th}$-$(2N)_{th}$ transducer elements successively emit the ultrasound beams.

8 Claims, 4 Drawing Sheets

(51) Int. Cl.
*G01S 15/89* (2006.01)
*A61B 8/08* (2006.01)

(56) References Cited

U.S. PATENT DOCUMENTS

| | | | | |
|---|---|---|---|---|
| 8,157,739 B2 * | 4/2012 | Angelsen | ............ | G01S 15/8922 600/447 |
| 2002/0007118 A1 * | 1/2002 | Adachi | ................ | B06B 1/0611 600/443 |
| 2002/0040189 A1 * | 4/2002 | Averkiou | ................. | A61B 8/06 600/458 |
| 2002/0067531 A1 * | 6/2002 | Hsiao | ................. | H04B 10/502 398/182 |
| 2002/0099290 A1 * | 7/2002 | Haddad | ............... | A61B 8/0825 600/443 |
| 2005/0228287 A1 * | 10/2005 | Little | ................. | G01S 7/52023 600/459 |
| 2008/0021324 A1 * | 1/2008 | Seto | ........................ | A61B 8/00 600/447 |
| 2009/0005684 A1 * | 1/2009 | Kristoffersen | ....... | A61B 8/4461 600/447 |
| 2010/0022887 A1 * | 1/2010 | Main | ........................ | A61B 8/06 600/454 |
| 2010/0030080 A1 * | 2/2010 | Suetoshi | ............... | A61B 5/4509 600/449 |
| 2010/0305443 A1 * | 12/2010 | Bartlett | .................... | A61B 8/00 600/443 |
| 2014/0088431 A1 | 3/2014 | Miyazawa | | |
| 2014/0116139 A1 * | 5/2014 | Endo | .................... | A61B 8/4494 73/584 |

FOREIGN PATENT DOCUMENTS

| | | | | |
|---|---|---|---|---|
| CN | 104414681 A | * | 3/2015 | ............... A61B 8/06 |
| TW | 201243371 | | 11/2012 | |

* cited by examiner

ULTRASOUND APPARATUS AND ULTRASOUND EMISSION METHOD

BACKGROUND

Technical Field

The disclosure relates to an ultrasound apparatus and an ultrasound emission method adapted to the ultrasound apparatus.

Description of Related Art

Ultrasound has been widely used in medical diagnosis, military radar system and rusting detection. In the medical diagnosis system, the ultrasound is often used in imaging internal body structures such as tendons, muscles, joints, vessels and internal organs. Images obtained by the ultrasound may clearly show the internal body, which help medical personnel to correctly diagnose illness or disease of a patient. Thereafter, appropriate treatment could be chosen and performed to the patient.

In a traditional medical ultrasound apparatus, during the ultrasound scanning of an object, ultrasound beams are outputted by a plurality of transducer elements in a probe to form a plane wave, and echoes of the plane wave are detected and recorded for generating the image of the internal structure of the object. However, when using the probe for ultrasound scanning, the wave strength at the beginning and the end of the ultrasound plane wave is usually weaker than the wave strength at the other parts of the ultrasound plane wave. This usually leads to inaccurate ultrasound detection.

Therefore, compensation should be made in order to put the wave strength of the plane wave in consistency. It is still a goal of effort for those technicians of the field to provide an efficient and accurate ultrasound detection.

SUMMARY

The disclosure is directed to an ultrasound apparatus and an ultrasound emission method, by which ultrasound detection is precisely and accurately performed.

An embodiment of the disclosure provides an ultrasound apparatus. The ultrasound apparatus includes an ultrasound probe, a transceiver circuit, a switch module and a processor. The ultrasound probe has a $1_{st}$ transducer element to a $M_{th}$ transducer element for respectively emitting ultrasound beams to form a plane wave, where M is a positive integer. The transceiver circuit has a $1_{st}$ transceiving channel to a $N_{th}$ transceiving channel, where N is a positive integer, and M is a multiple of N. The switch module is switched between the ultrasound probe and the transceiver circuit, and the processor controls the switch module and the transceiver circuit. During a scanning period, the processor controls the switch module to initially and respectively connect the $1_{st}$-$N_{th}$ transceiving channels to the $1_{st}$-$N_{th}$ transducer elements and controls the transceiver circuit to generate transmission signals, such that the $1_{st}$-$N_{th}$ transducer elements successively emit the ultrasound beams in response to the transmission signals from the $1_{st}$-$N_{th}$ transceiving channels. After the ultrasound beam is emitted by the $N_{th}$ transducer element, the processor controls the switch module to respectively connect the $1_{st}$-$N_{th}$ transceiving channels to the $(N+1)_{th}$-$(2N)_{th}$ transducer elements and controls the transceiver circuit to generate the transmission signals, such that the $(N+1)_{th}$-$(2N)_{th}$ transducer elements successively emit the ultrasound beams in response to the transmission signals from the $1_{st}$-$N_{th}$ transceiving channels.

In an embodiment of the disclosure, every two of the ultrasound beams that are successively emitted are separated in time by an interval.

In an embodiment of the disclosure, operation of the switch module as to respectively connect the $1_{st}$-$N_{th}$ transceiving channels to the $(N+1)_{th}$-$(2N)_{th}$ transducer elements is performed during the interval.

In an embodiment of the disclosure, when every two adjacent transducer elements are apart with a distance 1, for emitting the plane wave with an incident angle θ, the interval is: interval=1×sin θ/V, wherein V is a velocity of ultrasound.

In an embodiment of the disclosure, when M equals to 2N, after the ultrasound beam is emitted by the $(2N)_{th}$ transducer element, the processor controls the switch module to respectively connect the $1_{st}$-$N_{th}$ transceiving channels to the $1_{st}$-$N_{th}$ transducer elements for detecting echoes of the ultrasound beams in rest of the scanning period. When the echoes of the ultrasound beams are detected, reception signals are generated by the $1_{st}$-$N_{th}$ transducer elements and transmitted to the $1_{st}$-$N_{th}$ transceiving channels. The reception signals are further transferred to Low-Voltage Differential Signaling (LVDS) signals by the transceiver circuit, and the LVDS signals are then sent to the processor.

In an embodiment of the disclosure, the switch module comprises at least one high voltage switch, and each of the at least one high voltage switch is switched between a portion of the transducer elements and a portion of the transceiving channels.

Another embodiment of the disclosure provides an ultrasound emission method, adapted to an ultrasound apparatus for emitting a plane wave during a scanning period. The ultrasound apparatus has an ultrasound probe, a transceiver circuit and a switch module switched between the ultrasound probe and the transceiver circuit. The ultrasound probe has a $1_{st}$ transducer element to a $M_{th}$ transducer element for respectively emitting ultrasound beams to form the plane wave, the transceiver circuit has a $1_{st}$ transceiving channel to a $N_{th}$ transceiving channel, M, N are positive integers, and M is a multiple of N. The method includes the following steps. The switch module is controlled to initially and respectively connect the $1_{st}$-$N_{th}$ transceiving channels to the $1_{st}$-$N_{th}$ transducer elements. The transceiver circuit is controlled to generate transmission signals. The ultrasound beams are successively emitted by the $1_{st}$-$N_{th}$ transducer elements in response to the transmission signals from the $1_{st}$-$N_{th}$ transceiving channels. After the ultrasound beam is emitted by the $N_{th}$ transducer element, the switch module is controlled to respectively connect the $1_{st}$-$N_{th}$ transceiving channels to the $(N+1)_{th}$-$(2N)_{th}$ transducer elements. The transceiver circuit is controlled to generate transmission signals. The ultrasound beams are successively emitted by the $(N+1)_{th}$-$(2N)_{th}$ transducer elements in response to the transmission signals from the $1_{st}$-$N_{th}$ transceiving channels.

According to the above description, in the ultrasound apparatus and the ultrasound emission method, through the operation of the switch module, the total number of the emitted ultrasound beams during a single scanning period is at least twice of the number of the transceiving channels. Thus, energy of the emission is increased, so the Signal-to-Noise Ratio (SNR) has been raised, such that the ultrasound detection is more precise and accurate, and the quality of the ultrasound image is also improved. Further, the total cycle time for a succeed scanning could be shortened, so as to lower the power consumption on ultrasound detection.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

Figure 1:
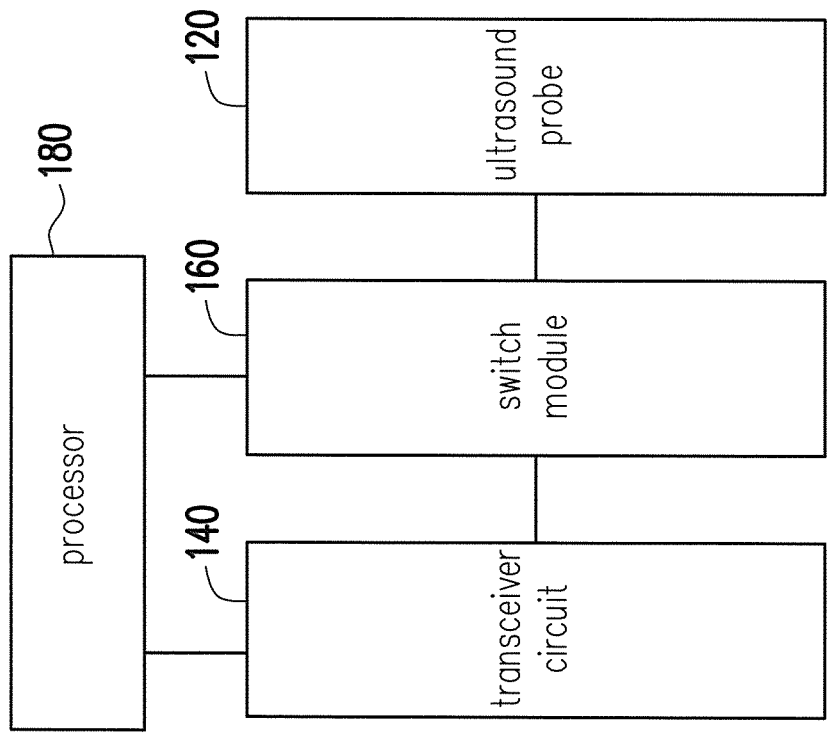
FIG. 1 is a block diagram illustrating an ultrasound apparatus according to an embodiment of the present disclosure.

Reference will now be made in detail to the present preferred embodiments of the disclosure, examples of which are illustrated in the accompanying drawings. Wherever possible, the same reference numbers are used in the drawings and the description to refer to the same or like parts.

FIG. 1 is a block diagram illustrating an ultrasound apparatus according to an embodiment of the present disclosure. Referring to FIG. 1, in the present embodiment of the present disclosure, the ultrasound apparatus 100 includes an ultrasound probe 120, a transceiver circuit 140, a switch module 160 and a processor 180. The switch module 160 is switched between the ultrasound probe 120 and the transceiver circuit 140. The processor 180 is connected to the switch module 160 and the transceiver circuit 140, and thereby controls the switch module 160 and the transceiver circuit 140 for the ultrasound emission and detection. In an embodiment of the disclosure, the ultrasound apparatus 100 may be implemented in an electronic apparatus with computation ability, such as a personal computer, a laptop computer, a tabular computer, a server and a smart device, but it is not limited herein.

Figure 2:
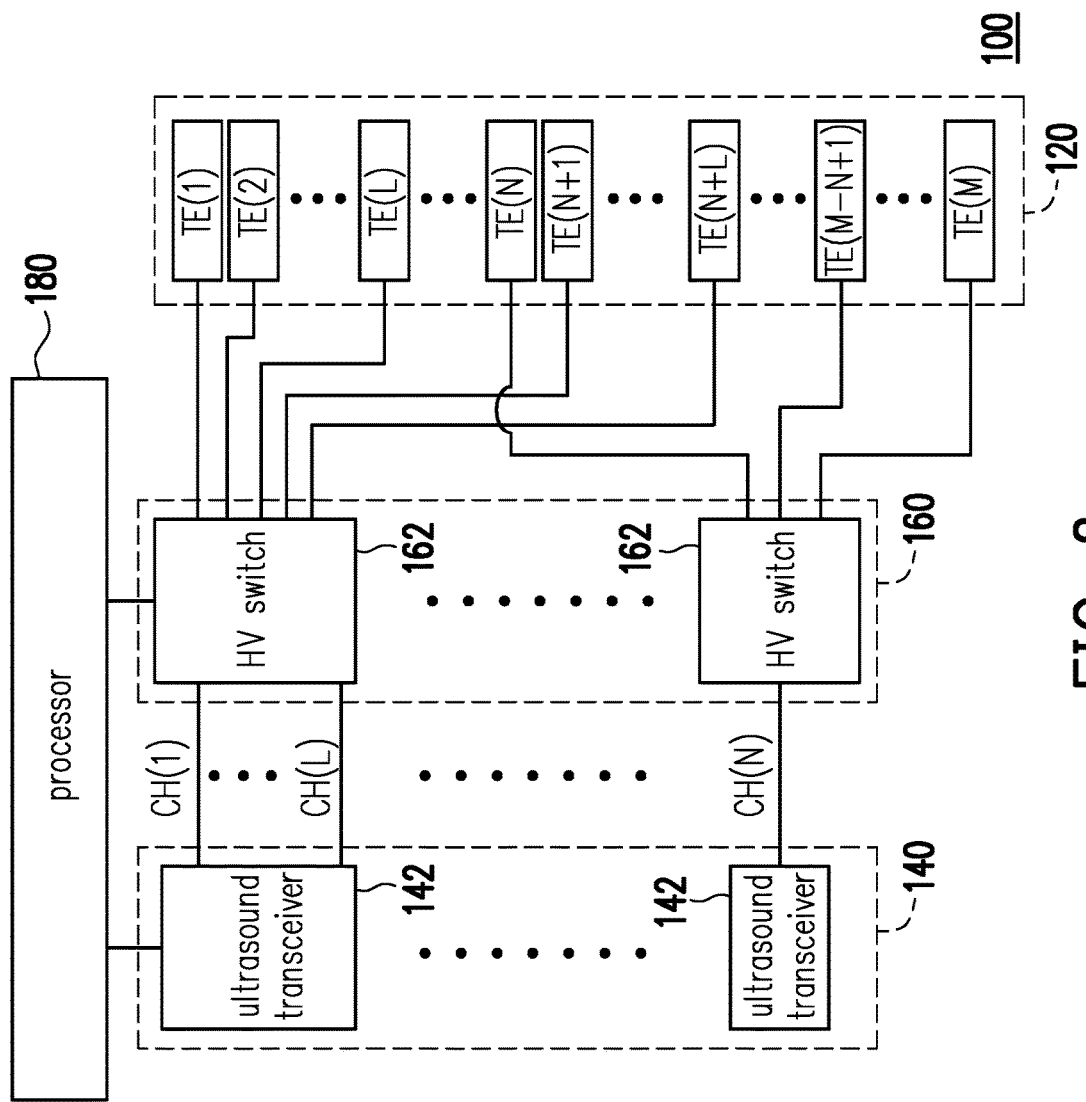
FIG. 2 is a detailed diagram illustrating an ultrasound apparatus according to an embodiment of the present disclosure.

In an embodiment of the present disclosure, the ultrasound probe 120 includes a plurality of transducer elements, which emits ultrasound waves and receives echoes of the ultrasound waves. FIG. 2 is a detailed diagram illustrating an ultrasound apparatus according to an embodiment of the present disclosure. Referring to FIG. 1 and FIG. 2, in the present embodiment, a $1_{st}$ transducer elements to a $M_{th}$ transducer elements TE(1)-TE(M) of the ultrasound probe 120 are arranged in a line, where M is a positive number, but the arrangement of the transducer elements TE(1)-TE(M) is not limited herein.

In the present embodiment, every two adjacent transducer elements, such as the transducer element TE(1) and the transducer element TE(2), are apart with a distance 1. The distance 1 is determined in accordance with the design of the ultrasound probe 120, and it could be several millimeters (mm) or less, though it is not limited herein. By respectively applying voltages (also called transmission signals) to the transducer elements TE(1)-TE(M), each of the transducer elements TE(1)-TE(M) is driven to output ultrasound beam, and those ultrasound beams are combined to form a plane wave traveling along a preferred direction.

After the emission of the ultrasound waves, the $1_{st}$ transducer elements to the $M_{th}$ transducer elements TE(1)-TE(M) of the ultrasound probe 120 are further configured to listen for echoes that are produced when the emitted ultrasound waves are reflected by objects. Reception signals are generated by the transducer elements TE(1)-TE(M) when detecting and receiving the echoes.

Referring to FIG. 1 and FIG. 2, in an embodiment of the present disclosure, the transceiver circuit 140 includes a plurality of ultrasound transceivers 142 and a $1_{st}$ transceiving channel to a $N_{th}$ transceiving channel CH(1)-CH(N), where N is a positive integer, and M is a multiple of N. Each of the ultrasound transceivers 142 may provide several transceiving channels. In the present embodiment shown in FIG. 2, the ultrasound transceivers 142 are octal ultrasound transceivers which respectively provides 8 transceiving channels CH(1)-CH(8), . . . , CH(N−8)-CH(N). However, the embodiment is not intended to limit the number of the transceiving channels for each of the ultrasound transceivers 142. In other embodiments, the each of the ultrasound transceivers 142 may provide various number of the transceiving channels.

In the present embodiment, the $1_{st}$ transceiving channel to the $N_{th}$ transceiving channel CH(1)-CH(N) are responsible for generating and transmitting transmission signals to the ultrasound probe 120 under the control of the processor 180. The transmission signals are the voltage pulses that applied to the transducer elements TE(1)-TE(M) of the probe 120. Further, when receiving reception signals from the ultrasound probe 120 in response to the echoes of the ultrasound, the $1_{st}$ transceiving channel to the $N_{th}$ transceiving channel CH(1)-CH(N) correspondingly transforms the reception signals to Low-Voltage Differential Signaling (LVDS) signals, and then send the LVDS signals to the processor 180.

Referring to FIG. 1 and FIG. 2, in an embodiment of the present disclosure, the switch module 160 includes at least one high voltage (HV) switch 162. In the embodiment, the high voltage switch 162 may be a multiplexer, however, the embodiment is not intended to limit the implement of the high voltage switch 162. Each high voltage switch 162 switches the connections between a portion of the transducer elements TE(1)-TE(M) and a portion of the transceiving channels CH(1)-CH(N) For example, the high voltage switch 162 switches the connection between the transducer elements TE(1)-TE(L), TE(N+1)-TE(N+L) and the transceiving channels CH(1)-CH(L), where L is a positive integer less than N.

Referring to FIG. 1 and FIG. 2, the processor 180 is a central processing unit (CPU), a programmable microprocessor, a digital signal processor (DSP), a programmable controller, an application specific integrated circuit (ASIC), a Field-programmable gate array (FPGA) or a programmable logic device (PLD), for example, but not limited thereto.

In an embodiment of the disclosure, the ultrasound apparatus 100, for example, further includes a storage unit (not shown) and an input/output (I/O) interface (not shown). The storage unit is, for example, a hard disk, a random access memory (RAM) or a similar device having a storage function for storing various messages, programs and data. The I/O interface of the ultrasound apparatus 100 is, for example, a universal serial bus (USB) port, a wireless communication device or a similar device having a communication function for communicating with other apparatuses and devices.

Figure 3:
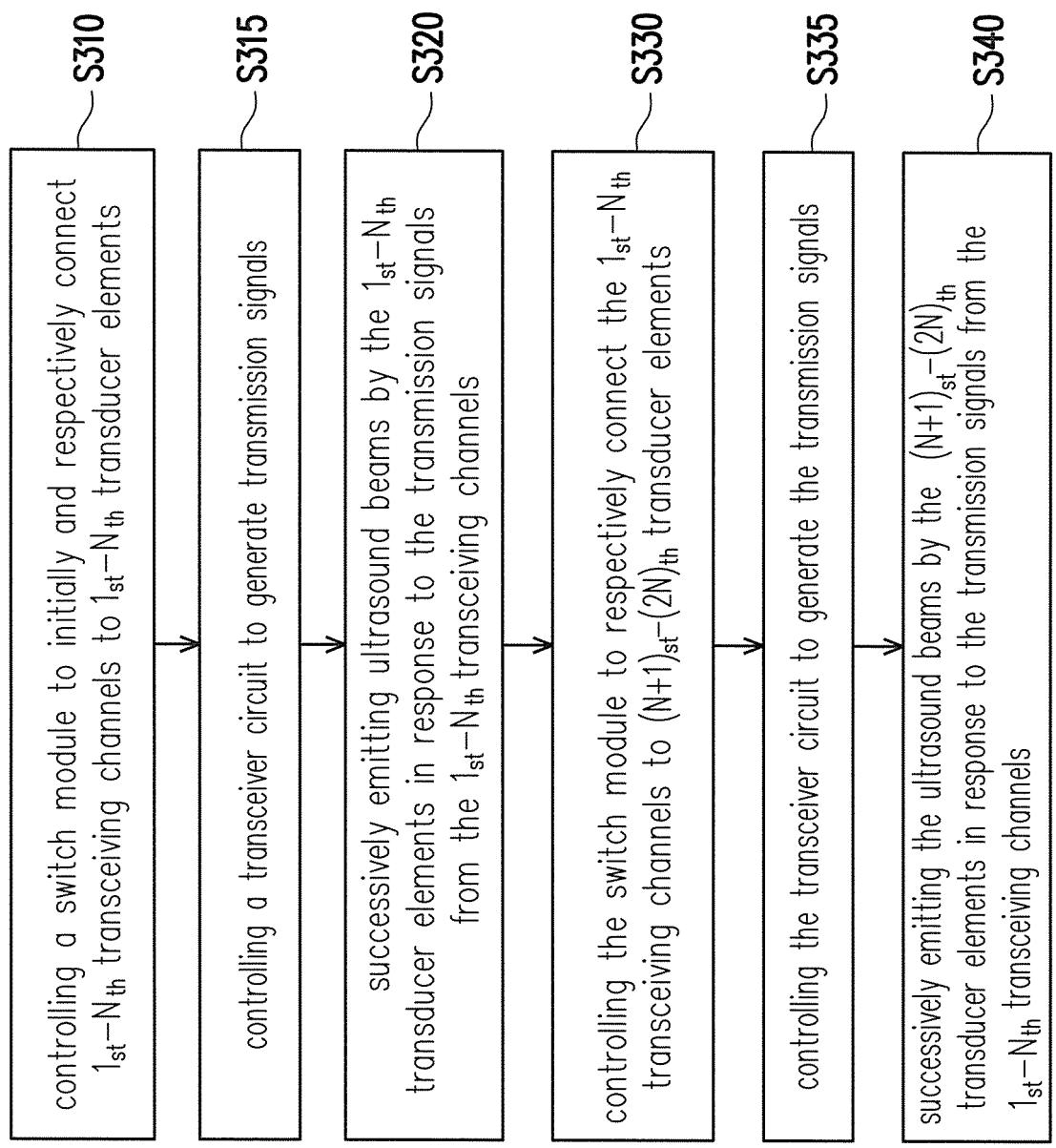
FIG. 3 is a flowchart illustrating an ultrasound emission method according to an embodiment of the present disclosure.

FIG. 3 is a flowchart illustrating an ultrasound emission method according to an embodiment of the present disclosure. In the present embodiment, the ultrasound emission method is, for example, adapted to the ultrasound apparatus 100 shown in FIG. 1 and FIG. 2. Referring to FIG. 1, FIG. 2, and FIG. 3, during a scanning period, the switch module 160 is controlled by the processor 180 to initially and respectively connect the $1_{st}$-$N_{th}$ transceiving channels CH(1)-CH(N) to the $1_{st}$-$N_{th}$ transducer elements TE(1)-TE(N) (step S310). After the $1_{st}$-$N_{th}$ transceiving channels CH(1)-CH(N) are connected to the $1_{st}$-$N_{th}$ transducer elements TE(1)-TE(N), the processor 180 controls the transceiver circuit 140 to generate transmission signals (step S315) by transmitting control signals to the transceiver circuit 140. The transmission signals are further sent to the ultrasound probe 120 from the $1_{st}$-$N_{th}$ transceiving channels CH(1)-CH(N) of the transceiver circuit 140 through the switch module 160.

In response to the transmission signals from the $1_{st}$-$N_{th}$ transceiving channels CH(1)-CH(N), the ultrasound beams are successively emitted by the $1_{st}$-$N_{th}$ transducer elements TE(1)-TE(N) (step S320). It should be noted that, in an embodiment of the present disclosure, a time delay is adopted in successively emitting the ultrasound beams. In other words, every two of the ultrasound beams that are successively emitted, such as the ultrasound beams emitted by the $1_{st}$ transducer element TE(1) and the $2_{nd}$ transducer element TE(2), are separated in time by an interval.

Figure 4:
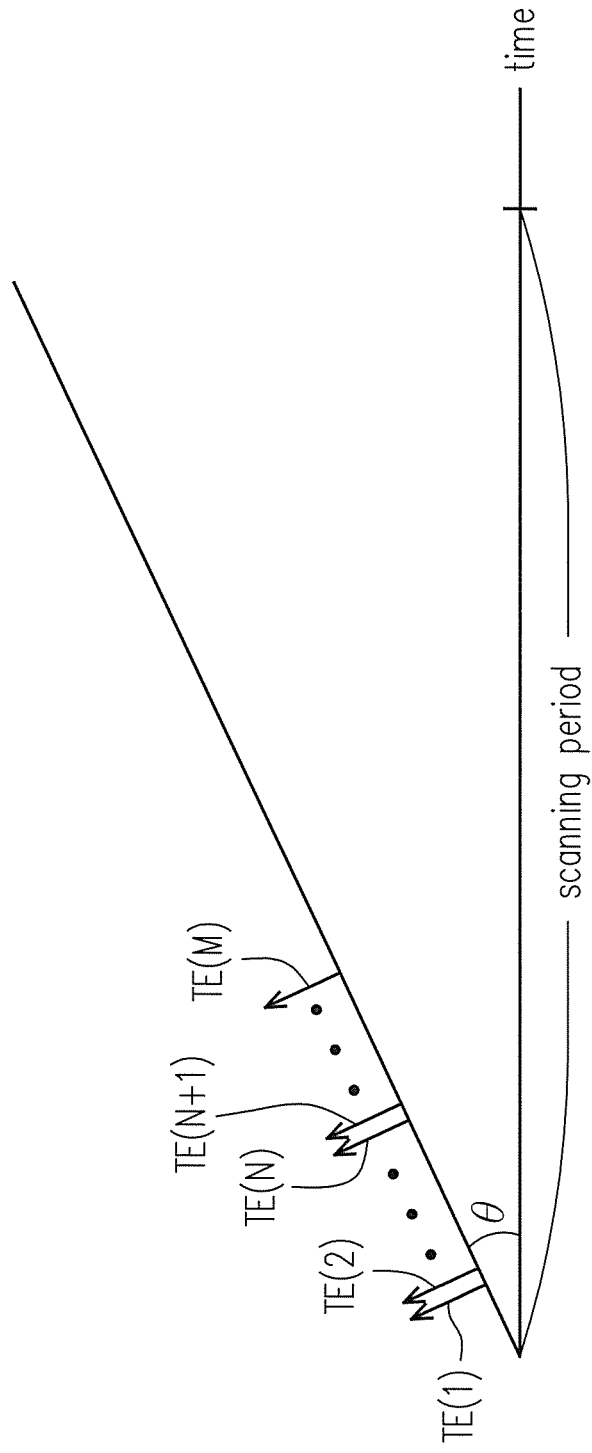
FIG. 4 is a schematic diagram of emitting a plane wave according to an embodiment of the present disclosure.

FIG. 4 is a schematic diagram of emitting a plane wave according to an embodiment of the present disclosure. Referring to FIG. 4, when every two adjacent transducer elements, such as the $1_{st}$ transducer element TE(1) and the $2_{nd}$ transducer element TE(2), are apart with a distance 1, for emitting the plane wave with an incident angle θ, the interval mentioned above is shown as below.

$$\text{interval} = 1 \times \sin \theta / V \quad (1)$$

It should be noted that, V is a velocity of ultrasound which is approximately 1540 meters per second (m/s). Thus, for example, the ultrasound beam emitted by the $2_{nd}$ transducer element TE(2) is subsequent to the ultrasound beam emitted by the $1_{st}$ transducer element TE(1) for one interval mentioned above in time.

Referring to FIG. 1 to FIG. 4, after the ultrasound beam is emitted by the $N_{th}$ transducer element, during the scanning period, the switch module 160 is controlled by the processor 180 to respectively connect the $1_{st}$-$N_{th}$ transceiving channels CH(1)-CH(N) to the $(N+1)_{th}$-$(2N)_{th}$ transducer elements TE(N+1)-TE(2N) (step S330). Then, the processor 180 controls the transceiver circuit 140 to generate the transmission signals (step S335) by transmitting the control signals to the transceiver circuit 140. The transmission signals are further sent to the ultrasound probe 120 from the $1_{st}$-$N_{th}$ transceiving channels CH(1)-CH(N) of the transceiver circuit 140 through the switch module 160, such that the ultrasound beams are successively emitted by the $(N+1)_{th}$-$(2N)_{th}$ transducer elements TE(N+1)-TE(2N) (step S340) in response to the transmission signals from the $1_{st}$-$N_{th}$ transceiving channels CH(1)-CH(N).

In an embodiment of the present disclosure, since the ultrasound beams that are successively emitted by the $N_{th}$ transducer element TE(N) and the $(N+1)_{th}$ transducer element TE(N+1) are also separated in time by the interval mentioned above, operation of the switch module 160 for respectively connecting the $1_{st}$-$N_{th}$ transceiving channels CH(1)-CH(N) to the $(N+1)_{th}$-$(2N)_{th}$ transducer elements TE(N+1)-TE(2N) should be performed during the interval.

In other words, the operation of the switch module 160 for respectively connecting the $1_{st}$-$N_{th}$ transceiving channels CH(1)-CH(N) to the $(N+1)_{th}$-$(2N)_{th}$ transducer elements TE(N+1)-TE(2N) should be completed before the emission of the ultrasound beam performed by the $(N+1)_{th}$ transducer element TE(N+1).

Through the ultrasound emission method illustrated above, during one single scanning period, the total number of the emitted ultrasound beams is at least twice of the number of the transceiving channels CH(1)-CH(N). Thus, energy of the emission is increased, and the SNR of the ultrasound plane wave has been raised.

In an embodiment of the present disclosure, when M equals to 2N as shown in FIG. 2, after the ultrasound beam is emitted by the $(2N)_{th}$ transducer element TE(2N), the processor 180 controls the switch module 160 to respectively connect the $1_{st}$-$N_{th}$ transceiving channels CH(1)-CH(N) to the $1_{st}$-$N_{th}$ transducer elements TE(1)-TE(N) for detecting echoes of the ultrasound beams in rest of the scanning period. When the echoes of the ultrasound beams are detected, the reception signals are generated by the $1_{st}$-$N_{th}$ transducer elements TE(1)-TE(N) and transmitted to the $1_{st}$-$N_{th}$ transceiving channels CH(1)-CH(N). The reception signals are further transferred to LVDS signals by the transceiver circuit 140, and the LVDS signals are then sent to the processor 180.

However, in another embodiment of the present disclosure, when M equals to 3N, the processor 180 controls switch module 160 to connect the $1_{st}$-$N_{th}$ transceiving channels CH(1)-CH(N) to the $1_{st}$-$N_{th}$ transducer elements, the $(N+1)_{st}$-$(2N)_{th}$ transducer elements, and the $(2N+1)_{st}$-$(3N)_{th}$ transducer elements in serial. After the ultrasound beam is emitted by the $(3N)_{th}$ transducer element, the processor 180 controls the switch module 160 to respectively connect the $1_{st}$-$N_{th}$ transceiving channels CH(1)-CH(N) to the $1_{st}$-$N_{th}$ transducer elements TE(1)-TE(N) for detecting echoes of the ultrasound beams in rest of the scanning period.

In the present disclosure, the numbers and the relationship of M and N may be varied. However, from the above description, the corresponding operation of the ultrasound apparatus 100 and the ultrasound emission method could still be deduced even when M and N are changed, so those are not illustrated herein.

A design of the ultrasound apparatus 100 in an embodiment of the present disclosure is provided below. In this embodiment, M is 128, N is 64, so the number of the transducer elements is twice of the number of the transceiving channels. Further, if the number of the high voltage switch 162 is 4, then L is 16. One single scanning period may be 200 microseconds (μs), and ultrasound emission performed by all the transducer elements TE(1)-TE(M) may only cost a few microseconds (μs). However, it should be noted that, the design of the ultrasound apparatus 100 may be varied in corresponding to the practical requirement on the ultrasound detection.

In summary, in the ultrasound apparatus and the ultrasound emission method, through the operation of the switch module, the total number of the emitted ultrasound beams during a single scanning period is at least twice of the number of the transceiving channels. Thus, energy of the emission is increased, so the Signal-to-Noise Ratio (SNR) has been raised, such that the ultrasound detection is more precise and accurate, and the quality of the ultrasound image is also improved. Further, the total cycle time for a succeed scanning could be shortened, so as to lower the power consumption on ultrasound detection.

It will be apparent to those skilled in the art that various modifications and variations can be made to the structure of the disclosure without departing from the scope or spirit of the disclosure. In view of the foregoing, it is intended that the disclosure cover modifications and variations of this invention provided they fall within the scope of the following claims and their equivalents.

What is claimed is:

1. An ultrasound apparatus, comprising:
an ultrasound probe, having M transducer elements for respectively emitting ultrasound signals to form a plane wave, where M is a positive integer;
a transceiver circuit, having N transceiving channels, where N is a positive integer, and M is a multiple of N;
at least one switch configured to switch between the ultrasound probe and the transceiver circuit; and
a processor configured to control the at least one switch and the transceiver circuit, wherein during a scanning period, the processor controls the at least one switch to initially and respectively conned the transceiving channels to a first serial group of N transducer elements and controls the transceiver circuit to generate first transmission signals, wherein the first serial group of N transducer elements successively emit first ultrasound signals of the ultrasound signals through the N transceiving channels in response to the first transmission signals, and in response to the last one of the first ultrasound signals of the ultrasound signals emitted by the $N_{th}$ transducer element of the first serial group, the processor controls the at least one switch to respectively connect the N transceiving channels to a second serial group of N transducer elements of the transceiver circuit and controls the transceiver circuit to generate second transmission signals, wherein the second serial group of N transducer elements successively emit second ultrasound signals of the ultrasound signals in response to the second transmission signals from the N transceiving channels, wherein the transceiving channels connect to serial groups of N transducer elements and sequentially emit the ultrasound signals until the ultrasound signals are emitted by the $M_{th}$ transducer element, wherein
in response to the last one of the ultrasound signals emitted by the $M_{th}$ transducer element, the processor controls the at east one switch to respectively connect the N transceiving channels to the first serial group of N transducer elements to detect echoes corresponding to the first transmission signals after the scanning period.

2. The ultrasound apparatus according to claim 1, wherein every two of ultrasound signals, which are successively emitted from two adjacent transducer elements, are separated in time by an interval.

3. The ultrasound apparatus according to claim 2, wherein operation of the at least one switch configured to respectively connect the N transceiving channels to the second serial group of N transducer elements is performed during a second interval, wherein the second interval is equal to the interval.

4. The ultrasound apparatus according to claim 1, wherein in response to the echoes detected by the first serial group, reception signals corresponding to the echoes are generated by the first serial group of N transducer elements and transmitted to the N transceiving channels, the reception signals are further transferred to Low-Voltage Differential Signaling (LVDS) signals by the transceiver circuit, and the LVDS signals are then received by the processor.

5. The ultrasound apparatus according to claim 1, wherein the at least one switch comprises at least one high voltage switch, and each of the at least one high voltage switch is switched between a portion of the M transducer elements and a portion of the N transceiving channels.

6. An ultrasound emission method, adapted to an ultrasound apparatus for emitting a plane wave during a scanning period, the ultrasound apparatus has an ultrasound probe, a transceiver circuit and at least one switch configured to switch between the ultrasound probe and the transceiver circuit, the ultrasound probe has M transducer elements for respectively emitting ultrasound signals to form the plane wave, the transceiver circuit has N transceiving channels, M and N are positive integers, and M is a multiple of N, the method comprising:
controlling the at least one switch to initially and respectively connect the N transceiving channels to a first serial group of N transducer elements;
controlling the transceiver circuit to generate first transmission signals;
successively emitting first ultrasound signals of the ultrasound signals by the first serial group of N transducer elements through the N transceiving channels in response to the first transmission signals;
in response to the last one of the first ultrasound signals of the ultrasound signals is emitted by the $N_{th}$ transducer element of the first serial group, controlling the at least one switch to respectively connect the N transceiving channels to a second serial group of N transducer elements of the transceiver circuit;
controlling the transceiver circuit to generate second transmission signals;
successively emitting second ultrasound signals of the ultrasound beams by the second serial group of N transducer elements in response to the second transmission signals from the N transceiving channels, wherein the transceiving channels connect to serial groups of N transducer elements and sequentially emit the ultrasound signals until the ultrasound signals are emitted by the $M_{th}$ transducer element; and
in response to the last one of the ultrasound signals emitted by the $M_{th}$, transducer element, controlling the at least one switch to respectively connect the N transceiving channels to the first serial group of N transducer elements to detect echoes corresponding to the first transmission signals after the scanning period.

7. The method according to claim 6, wherein every two of ultrasound signals, which are successively emitted from two adjacent transducer elements, are separated in time by an interval.

8. The method according to claim 7, wherein step of controlling the at least one switch to respectively connect the N transceiving channels to the second serial group of N transducer elements is performed during a second interval, wherein the second interval is equal to the interval.

* * * * *